United States Patent [19]

Matsumura

[11] Patent Number: 4,917,458
[45] Date of Patent: Apr. 17, 1990

[54] CORNEA SHAPE MEASURING APPARATUS

[75] Inventor: Isao Matsumura, Yokosuka, Japan

[73] Assignee: Canon Kabushiki Kaisha, Tokyo, Japan

[21] Appl. No.: 390,506

[22] Filed: Aug. 1, 1989

Related U.S. Application Data

[63] Continuation of Ser. No. 53,483, May 26, 1997, abandoned.

[30] Foreign Application Priority Data

Jun. 9, 1986 [JP] Japan ............................... 61-133287

[51] Int. Cl.$^4$ ............................................. A61B 3/10
[52] U.S. Cl. ..................................... 354/212; 351/247
[58] Field of Search ..................... 351/212, 246, 247

[56] References Cited

U.S. PATENT DOCUMENTS

| | | | |
|---|---|---|---|
| 4,159,867 | 7/1979 | Achatz | 351/212 |
| 4,256,385 | 3/1981 | Cohen et al. | 351/212 |
| 4,666,269 | 5/1987 | Nakamura et al. | 351/212 |
| 4,692,003 | 9/1987 | Adachi et al. | 351/212 |

*Primary Examiner*—Rodney B. Bovernick
*Attorney, Agent, or Firm*—Fitzpatrick, Cella, Harper & Scinto

[57] ABSTRACT

A cornea shape measuring apparatus which is provided with first and second substantially ring-like index marks disposed at different positions in the direction of the optic axis and projected onto the cornea of an eye to be examined and in which the corneal reflection images of the first and second index marks are detected by a first position detector and the shape of the cornea is measured without depending on the working distance.

13 Claims, 2 Drawing Sheets

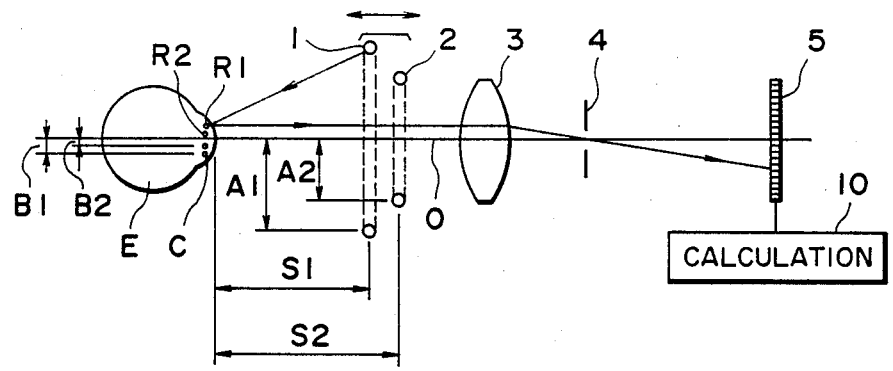
FIG. 1A
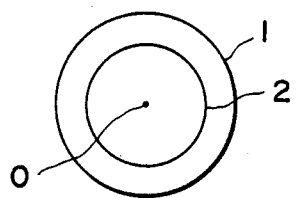     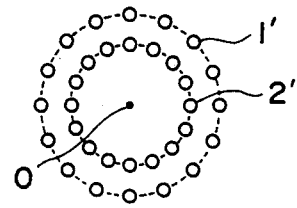
FIG. 1B     FIG. 1C
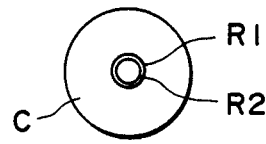     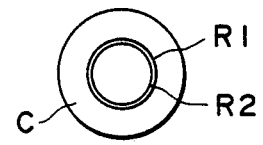
FIG. 2     FIG. 3
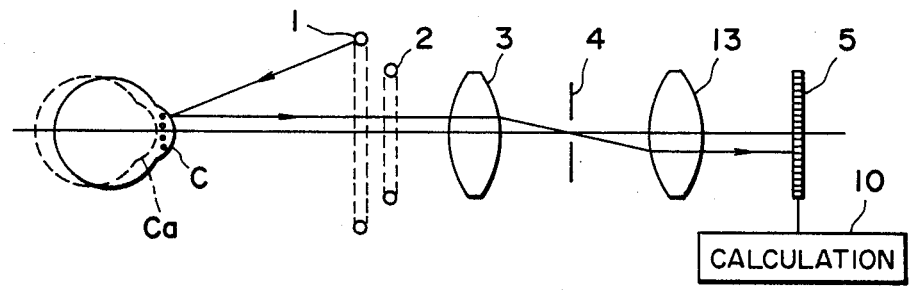
FIG. 4

CORNEA SHAPE MEASURING APPARATUS

This application is a continuation of application Ser. No. 07/053,483 filed May 26, 1987 now abandoned.

BACKGROUND OF THE INVENTION

1. Field of the Invention

This invention relates to a cornea shape measuring apparatus for ophthalmology in which index marks are projected onto the cornea of an eye to be examined and the reflected image by the cornea is measured to thereby measure the shape of the cornea.

2. Related Background Art

Heretofore, it has usually been the case with a cornea shape measuring apparatus of this type that a ring-like index mark image, i.e., a Mire image, is projected onto the cornea of an eye to be examined and the size or distortion of a reflected image formed by corneal reflection is measured and the radius of curvature of the cornea is calculated.

However, in such a prior-art system, if the spacing between the ring-like index mark and the cornea of the eye to be examined, i.e., the working distance, differs due to the setting error or the like of the apparatus during measurement, the size of the corneal reflection image varies and therefore, a measurement error occurs.

As a method of solving the problem that the size of the corneal reflection image varies depending on the adjustment of such working distance to cause the occurrence of a measurement error, it has been proposed to project the ring-like index mark substantially from infinity through a ring-like cylindrical lens as described in U.S. Application Ser. No. 416,355, U.S. Application Ser. No. 520,217 and U.S. Application Ser. No. 543,041 all now abandoned.

Generally, however, the use of a ring-like cylindrical lens leads to an increased cost of manufacture.

Further, where various concentric index marks of different radii as described in U.S. Ser. No. 520,217 are projected to measure the shapes of the central and marginal portions of the cornea of the eye to be examined, it becomes impossible to make the apparatus compact in a direction perpendicular to the optic axis.

SUMMARY OF THE INVENTION

It is an object of the present invention to provide a cornea shape measuring apparatus in which the above-mentioned measurement error is prevented from occurring even for a readily moving eye to be examined by a low-cost simple construction.

It is also an object of the present invention to provide a cornea shape measuring apparatus which can simply measure the shapes of the central and marginal portions of the cornea of an eye to be examined while maintaining the compactness of the apparatus.

BRIEF DESCRIPTION OF THE DRAWINGS

FIGS. 1A, 1B and 1C show the optical arrangement of a first embodiment of the present invention.

FIGS. 2 and 3 illustrate ring reflected images.

FIG. 4 shows the optical arrangement of a second embodiment of the present invention.

DESCRIPTION OF THE PREFERRED EMBODIMENTS

Figure 5:
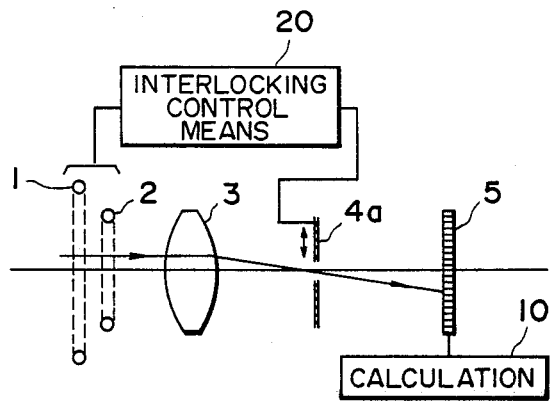
FIG. 5 shows the optical arrangement of a third embodiment of the present invention.

Referring to FIG. 1A, which shows an embodiment of a cornea shape measuring apparatus according to the present invention, letter E designates an eye to be examined and letter C denotes the cornea thereof. In the present embodiment, a first ring light source 1 and a second ring light source 2 which are two ring-like light sources are used as ring-like index marks projected toward the cornea C of the eye to be examined, that is, as shown in FIG. 1B or FIG. 1C an index mark on the same circumference centered at the optic axis 0 or a plurality of index marks provided on the same circumference (including also the case of four index marks, for example, in the directions of east, west, south and north illustrated in FIGS. 6 and 7). These two ring light sources 1 and 2 are concentric, but are disposed so that the distances S1 and S2 in the direction of the optic axis from the cornea C differ from each other. An imaging lens 3, an aperture step 4 and an area type CCD 5 are arranged in succession in opposed relationship with the eye E to be examined, and the aperture stop 4 is disposed at the rearward focus position of the imaging lens 3.

In FIG. 1A, the light from the first ring light source 1 is reflected by the cornea C and forms a first ring reflected image R1 (virtual image), which is imaged on the CCD via the imaging lens 3 and the aperture stop 4. On the other hand, the light from the second ring light source 2 is also reflected by the cornea C and forms a second ring reflected image R2 (virtual image), which is imaged on the CCD 5 via the imaging lens 3 and the aperture stop 4.

Assuming that the radii of the first and second ring light sources 1 and 2 are A1 and A2, respectively, that the radii of the first and second ring reflected images R1 and R2 are B1 and B2, respectively, that the radius of curvature of the cornea C is r and that the cornea C has been moved away from said predetermined position by a movement distance $\Delta S$ relative to the first ring light source 1 and the second ring light source 2, the following equations are established:

$$r = 2(S1 + \Delta S) \cdot B1/(A1 - B1) \tag{1}$$

$$r = 2(S2 + \Delta S) \cdot Bw/(A2 - B2) \tag{2}$$

From equations (1) and (2), $$\Delta S = \{B2(A1 - B1) \cdot S2 - B1(A2 - B2) \cdot S1\}/ \tag{3}$$

$$\{B1(A2 - B2) - B2(A1 - B1)\}$$

Figure 8:
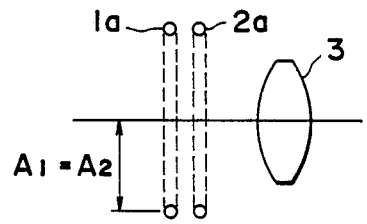
FIG. 8 shows a modification.

If this is substituted into equation (1), $$r = \{2B1/(A1 - B1)\}[S1 + \{B2 \cdot S2(A1 - B1) - B1 \cdot \tag{4}$$

$$S1(A2 - B2)\}/\{B1(A2 - B2) - B2(A1 - B1)\}] =$$

$$2B2 \cdot B1(S2 - S1)/\{A2 \cdot B1 - A1 \cdot B2\}$$

is derived and the cornea shape can be measured through a calculation unit 10. From this equation (4), it is apparent that the movement distance $\Delta S$ is an element having no relation to the measurement. The radii A1 and A2 of the ring light sources 1 and 2 may be made equal to each other as shown in FIG. 8.

Now, when the first ring light source 1 and the second light source 2 are brought close to the cornea C as a unit, the first and second ring reflected images R1 and R2 provided by corneal reflection become larger. FIGS. 2 and 3 show such a state, and FIG. 2 represents the first ring reflected image R1 and the second ring reflected image R2 when the distances from the first ring light source 1 and the second ring light source 2 to the cornea C are S1 and S2, respectively. Also, when the ring light sources 1 and 2 have been brought closer to the cornea C, the first ring reflected image R1 and the second ring reflected image R2 become larger as shown in FIG. 3. This means that if the distances to the cornea C are only changed, measurement in a wide range from the central portion to the marginal portion of the cornea C will become possible.

The imaging optical system for receiving the corneal reflection images used in the above-described embodiment can not only form an object side telecentric optical system as shown in FIG. 1A, but also can form an image side telecentric optical system by adding a relay lens 13 as shown in FIG. 4.

That is, the relay lens 13 is inserted between the aperture stop 4 and the CCD 5, and the aperture stop 4 is disposed at the rearward focus position of the imaging lens 3 and the forward focus position of the relay lens 13. According to this, even when the position of the cornea C has been displaced to a position indicated at Ca due to the setting error of the apparatus during measurement or when there is an error in the mounted position of the CCD 5, the sizes of the first and second ring reflected images R1 and R2 projected onto the CCD 5 remain invariable.

FIG. 5 shows an embodiment which uses, instead of the aperture stop 4 of FIG. 1A, a variable type aperture stop 4a having an aperture of variable size to increase the depth of focus when the first and second ring reflected images R1 and R2 are projected onto the CCD 5. Thus, the images can be projected with their blur being reduced even when the setting error in the direction of the optic axis has occurred and therefore, accurate measurement can be accomplished. In this case, it is also effective to enhance the brightness of the ring light sources 1 and 2 through interlocking control means 20 in accordance with the decrease in the quantity of light passing through the aperture stop 4a and interlock the ring light sources so as to follow the size of the aperture stop 4a.

The two ring light sources 1 and 2 may be an arrangement of a group of point sources of light which can be substantially regarded as a part of a ring, or the respective light sources may be used by rotating a single point source of light. Also, where measurement in a predetermined meridian direction is to be effected, a plurality of light sources facing in said meridian direction may be used.

Figure 6:
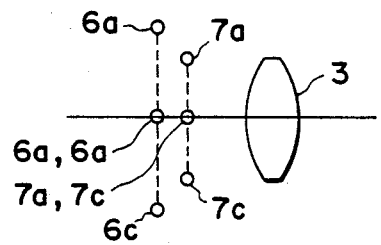
FIGS. 6 and 7 illustrate a fourth embodiment of the present invention.

FIG. 6 shows an example of such arrangement. Four point-like light sources 6a, 6b, 6c and 6d each comprising a light-emitting diode or the like are disposed as first index marks in meridian directions orthogonal to one another in a first plane lying at a distance S1 (the directions of east, west, south and north), and correspondingly thereto, four point-like light sources 7a, 7b, 7c and 7d are disposed as second index marks in meridian directions orthogonal to one another in a second plane lying at a distance S2 (the directions of east, west, sourth and north).

Figure 7:
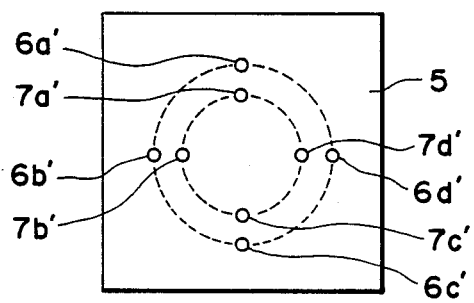

FIG. 7 shows light source images $6a'$-$6d'$ and $7a'$-$7d'$ projected onto the area type CCD 5. When such an arrangement is used, if the radius of curvature of the cornea is great, the spacing between corresponding ones of the light source images $6a'$-$6d'$ and the light source images $7a'$-$7d'$ becomes great, and if the radius of curvature of the cornea is small, the spacing between corresponding ones of the light source images becomes small. If there is astigmatism of the cornea, rotation of the image position will occur. The cornea shape can be calculated from this information.

I claim:

1. A cornea shape measuring apparatus, comprising:
   first and second substantially ring-like index marks adapted to be positioned a finite distance opposite an eye to be examined, said first index mark being adapted to be spaced from said second index mark in a direction of an optic axis;
   an imaging optical system for receiving corneal reflection images of said first and second index marks;
   a light position detector adapted to be provided on an image surface of said imaging optical system; and
   calculating means for calculating the radius of curvature of the cornea on the basis of: (i) distance between said first index mark and said second index mark in the direction of the optic axis; (ii) radii of the images of said first and second index marks; and (iii) radii of said first and second index marks.

2. A cornea shape measuring apparatus according to claim 1, wherein said first and second index marks are concentric ring-like index marks.

3. A cornea shape measuring apparatus according to claim 1, wherein said first and second index marks are integral with each other and displaceable in the direction of the optic axis.

4. A cornea shape measuring apparatus according to claim 1, wherein at least one of said first and second index marks is a ring-like light source.

5. A cornea shape measuring apparatus according to claim 4, wherein said first and second index marks are two ring-like light sources.

6. A cornea shape measuring apparatus according to claim 1, wherein said first and second index marks are point-like light sources disposed on predetermined circumferences in two different planes in the direction of the optic axis and in a plurality of predetermined meridian directions.

7. A cornea shape measuring apparatus according to claim 6, wherein said first and second index marks are disposed in the directions of east, west, south and north.

8. A cornea shape measuring apparatus according to claim 1, wherein said imaging optical system is an object side telecentric optical system provided with stop on the focal plane thereof.

9. A cornea shape measuring apparatus according to claim 8, wherein said imaging optical system includes an image side telecentric optical system.

10. A cornea shape measuring apparatus according to claim 8, wherein the aperture of said stop is variable in size.

11. A cornea shape measuring apparatus according to claim 10, wherein the brightness of said index marks is controlled in response to a variation in the size of the aperture of said stop.

12. A cornea shape measuring apparatus according to claim 1, wherein said first and second index marks differ in radius.

13. A cornea shape measuring apparatus according to claim 1, wherein said first and second index marks are equal in radius.

* * * * *

UNITED STATES PATENT AND TRADEMARK OFFICE
CERTIFICATE OF CORRECTION

PATENT NO. : 4,917,458

DATED : April 17, 1990

INVENTOR(S) : Isao Matsumura

It is certified that error appears in the above-identified patent and that said Letters Patent is hereby corrected as shown below:

Title page, item (63):
Related U.S. Application Data:

"Continuation of Ser. No. 53,483, May 26, 1997," should read
--Continuation of Ser. No. 53,483, May 26, 1987,--.

Column 3:

Line 2, "light source 2" should read --ring light source 2--.

Line 64, "sourth" should read --south--.

Column 4:

Line 50, "stop" should read --a stop--.

Signed and Sealed this

Twenty-third Day of June, 1992

Attest:

DOUGLAS B. COMER

*Attesting Officer*  *Acting Commissioner of Patents and Trademarks*